United States Patent [19]

Silverman

[11] 4,071,914

[45] Feb. 7, 1978

[54] MASTECTOMY PAD

[75] Inventor: Abe Silverman, Chicago, Ill.

[73] Assignee: Silveco Products, Inc., Chicago, Ill.

[21] Appl. No.: 762,940

[22] Filed: Jan. 26, 1977

[51] Int. Cl.² ............................ A61F 1/00; A41C 3/10
[52] U.S. Cl. .......................................... 3/36; 128/481
[58] Field of Search ..................... 3/36; 128/478–481;
2/267

[56] References Cited

U.S. PATENT DOCUMENTS

| 1,845,011 | 2/1932 | Yerkes | 3/36 |
|---|---|---|---|
| 2,482,297 | 9/1949 | Silverman | 3/36 |
| 2,738,510 | 3/1956 | Perl | 3/36 |
| 3,278,947 | 10/1966 | Silverman | 3/36 |
| 3,304,558 | 2/1967 | Mann | 3/36 |
| 3,464,418 | 9/1969 | Silverman | 128/481 |
| 3,502,083 | 3/1970 | Howard et al. | 128/480 |
| 3,576,037 | 4/1971 | Klein | 3/36 |
| 3,845,507 | 11/1974 | Kirby et al. | 3/36 |

FOREIGN PATENT DOCUMENTS

| 1,110,479 | 4/1968 | United Kingdom | 3/36 |

Primary Examiner—Ronald L. Frinks
Attorney, Agent, or Firm—Charles B. Cannon

[57] ABSTRACT

A mastectomy pad embodying an outer seamless molded fibrous material casing molded of high-loft non-woven bonded polyester fibrous material (such as Eastman KODEL) and including a generally conical preshaped body which is adapted to be worn in the conical-shaped cup of a brassiere or garment to simulate the breast of a woman who has had a mastectomy operation, and a laterally projecting tongue portion which is adapted to extend into the underarm area of the wearer to fill area from which tissue has been removed as an incident to the mastectomy operation. A generally conical preshaped molded closed foam rubber internal casing is arranged within the seamless molded polyester fibrous material outer casing and is molded of foam rubber and is weighted with a body of filler material which is preferably a mixture of particles of shredded foam rubber and sand. An outer protective fabric cover is arranged over and is stitched around its marginal edge portions to the outer marginal edge portions of the seamless molded polyester fibrous material outer casing outwardly of the outer marginal edge portion of the foam rubber internal casing so that the foam rubber internal casing is completely enclosed within the seamless molded outer fibrous material casing. A non-stretchable fabric attaching strap is attached to the weighted foam rubber internal casing and has attaching portions in the form of loops or tabs which are attached to a brassiere or garment worn by the user of the new mastectomy pad.

10 Claims, 24 Drawing Figures

MASTECTOMY PAD

BACKGROUND OF THE INVENTION

The prior art of mastectomy pads is exemplified by two of the applicant's earlier patents, namely, U.S. Pat. No. 2,482,297 granted to applicant on Sept. 20, 1949 on "Surgical Breast Pad," and U.S. Pat. No. 3,278,947 granted to the applicant on Oct. 18, 1966 on "Surgical Breast Pad." The mastectomy pads disclosed in the applicant's two earlier patents, referred to above, have enjoyed substantial success in the market and have, in general, functioned satisfactorily within their structural and functional applications. However, there has developed a need for a mastectomy pad which would combine all of the desirable characteristics of the applicant's two earlier mastectomy pads and certain additional novel features, advantages and improvements thereon, which will be referred to hereinafter.

Thus, there has been a need for a weighted mastectomy pad which embodies a seamless molded outer casing which would combine the desirable advantages and characteristics of the high-loft bonded polyester fibrous material of applicant's earlier U.S. Pat. No. 3,278,947, including softness; flexibility; ability to withstand repeated washings over a prolonged period of use; ability to adapt itself and the seamless molded outer casing thereof to brassiere cups of varying shapes; ability to impart to the wearer, as far as possible, a feeling of balance at both sides of the chest and resulting elimination of a tendency of the mastectomy patient to lean away from the body side at which the breast has been removed and toward the heavier body side at which the natural breast remains; a seamless molded front or outer side which eliminates the undesirable and unsightly appearance or indication of a seam at the front or outer side of the mastectomy pad to which some users of such mastectomy pads object for the reason that such a seam may be seen or otherwise observed from the front of the brassiere or other garment which may be worn by the user of such mastectomy pads; with the advantages of the foam rubber mastectomy pad of applicant's earlier U.S. Pat. No. 2,482,297 including its ability to retain its generally conical-shape while, at the same time, it has been desirable that such a mastectomy pad embody means for readily attaching it in position of use in a brassiere or garment and so that it will not shift from its desired position when in use; and so that it may readily be fastened to and removed from a brassiere or garment worn by the user of the new mastectomy pad.

OBJECTS

An object of the invention is to provide a new and improved weighted mastectomy pad which embodies a seamless molded outer casing and which is soft; flexible; comfortable in use; is washable in repeated washings over a pronlonged period of use; retains its molded form; readily adapts itself to brassiere cups of varying shapes; and in the preferred embodiment thereof has no visible or otherwise discernible seam or stitching at the front surface of the seamless molded outer casing thereof; will not shift from its desired position when in use; is readily attached to and removable from a brassiere or garment worn by the user; and has the other desirable advantages and characteristics referred to herein.

An additional object of the invention is to provide a new and improved seamless, molded and weighted mastectomy pad which combines the advantages of the applicant's prior high-loft bonded polyester fibrous material mastectomy pad and the applicant's prior foam rubber mastectomy pad, as disclosed in the applicant's two earlier patents hereinbefore referred to.

A further object of the invention is to provide a new and improved seamless, molded and weighted mastectomy pad which embodies a weighted closed foam rubber internal casing arranged within and completely enclosed by a seamless, molded polyester fibrous material outer casing which is stitched along its outer marginal edge portions to the outer marginal edge portions of a protective outer fabric cover, and with attaching means in the form of non-stretchable attaching loops or tabs attached to the weighted foam rubber internal casing and stitched to and projecting from the outer marginal edge portions of the seamless molded outer fibrous material casing and the protective outer fabric cover at the top and bottom of the new mastectomy pad for readily attaching it to and removing it from a shoulder strap and the underband of a brassiere or garment worn by the user and so that it will not shift from its desired position when in use.

Other objects will appear hereinafter.

DETAILED DESCRIPTION OF THE PREFERRED EMBODIMENT OF THE NEW MASTECTOMY PAD AS ILLUSTRATED IN FIGS. 1 TO 20, INCLUSIVE, OF THE DRAWINGS

A typical and preferred embodiment of the invention is illustrated in FIGS. 1 to 20, inclusive, of the drawings, wherein it is generally indicated at 30, and is shown as a left side mastectomy pad, as worn by a woman in the left side brassiere cup 31 of a brassiere or garment 32 which includes a right side brassiere cup 33, left and right shoulder straps 34 and 35, respectively, and an underband 36.

Figures 1, 2, 3, 5:
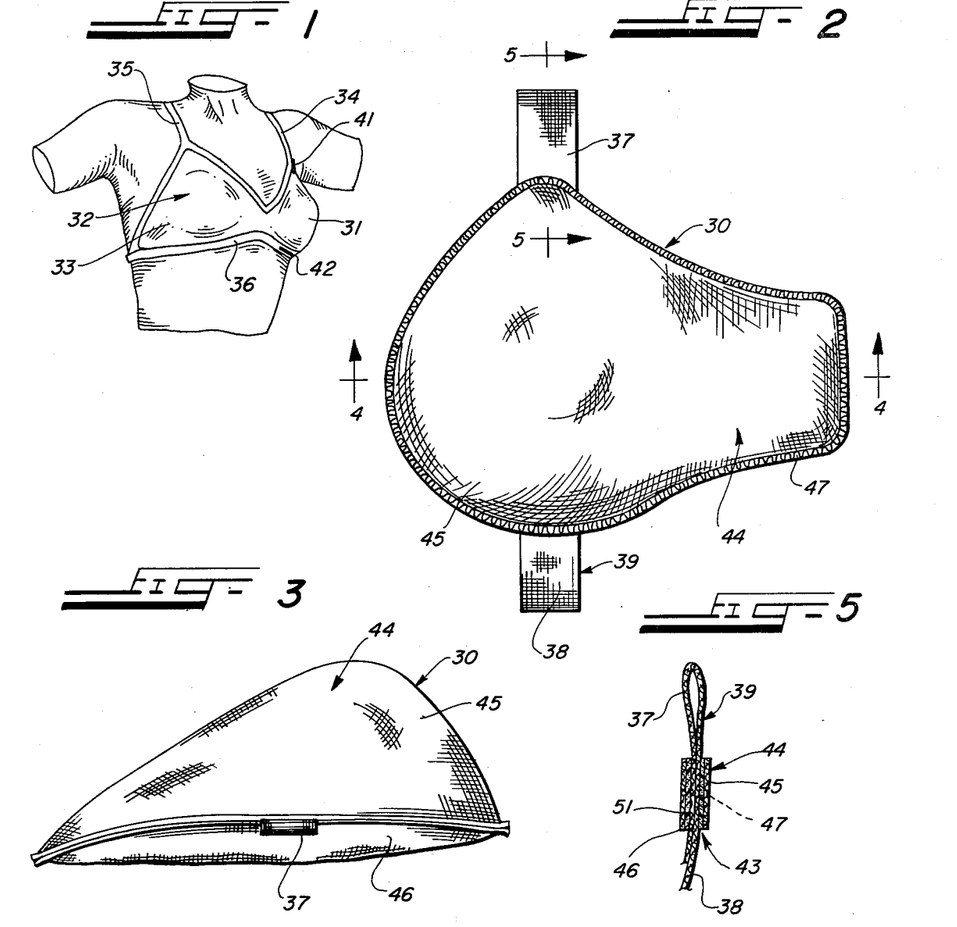
FIG. 1 is a perspective view illustrating the use of the new mastectomy pad, as worn inside of a brassiere by a woman who has had a mastectomy operation.
FIG. 2 is a top plan view of a preferred embodiment of the new mastectomy pad, which is shown as being in the form of a left side pad, and as seen from the outer or front side thereof.
FIG. 3 is a side or edge elevational view of the new mastectomy pad as shown in FIG. 2.
FIG. 5 is a fragmentary sectional view on line 5—5 in FIG. 2 illustrating the non-stretchable fabric attaching strap and attaching loops which are attached to the foam rubber internal casing, and illustrating the manner in which they are stitched to the marginal edge portions of the seamless molded fibrous material outer casing and to the marginal edge portions of the protective outer fabric cover, and illustrating the non-stretchable attaching loops or tabs which project from the top and bottom marginal edge portions of the new mastectomy pad for attaching it onto and removing it from the shoulder strap of a brassiere or garment in which the new mastectomy pad is worn by the user.

As shown in FIGS. 1 and 2, the new mastectomy pad 30 is attached in position of use in the left side brassiere cup 31 by top and bottom attaching means in the form of non-stretchable fabric attaching loops or tabs 37 and 38, respectively, which are formed as part of a non-stretchable fabric attaching strap 39 which is adhesively or otherwise attached to the inner or body side of a resilient closed foam rubber internal casing 40 which is embodied in the new mastectomy pad 30, and which will be described more fully hereinafter. Thus, the non-stretchable top attaching means or loop 37 may be attached by means of a safety pin 41, or the like, to the left shoulder strap 34 of the brassiere or garment 32 and the non-stretchable bottom attaching means or loop 38 may be attached to the underband 36 of the brassiere or garment 32 by a safety pin 42, or the like (FIG. 1).

Figures 4, 6, 7:
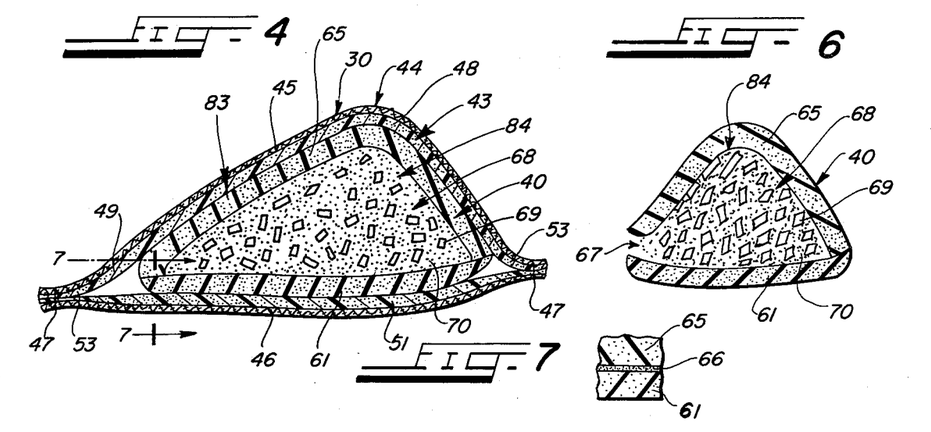
FIG. 4 is a central longitudinal sectional view on line 4—4 in FIG. 2.
FIG. 6 is a fragmentary sectional detail view illustrating the manner in which the weight means in the form of weighted filler material is inserted into the foam rubber internal casing.
FIG. 7 is an enlarged fragmentary sectional detail view, on lines 7—7 in FIG. 4 illustrating the manner in which the front or outer side component and the inner or body side component of the foam rubber internal casing are adhesively secured together.
Figure 8:
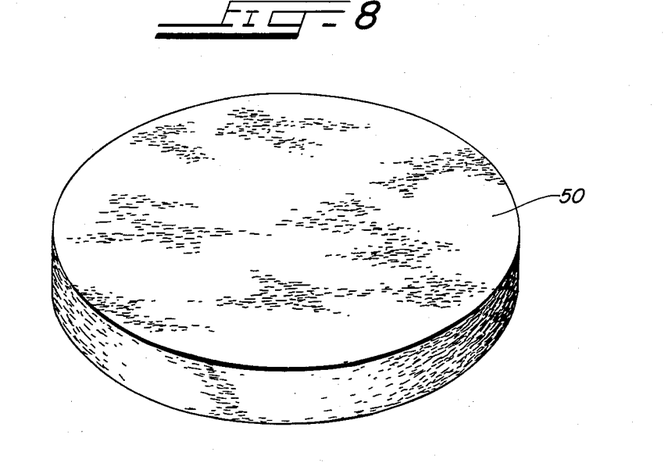
FIG. 8 is a perspective view of a circular panel of high-loft bonded polyester fibrous material which is molded into the form shown in FIG. 9 to provide the seamless molded front or outer side component of the seamless molded polyester fibrous material outer casing which is embodied in the preferred form of the new mastectomy pad.
Figure 9:
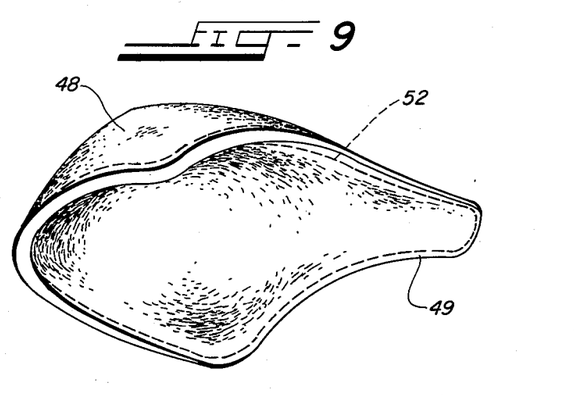
FIG. 9 is a bottom or body side perspective view of the molded seamless front or outer side component of the seamless molded polyester fibrous material outer casing as molded from the circular panel of the polyester fibrous material shown in FIG. 8.

The new mastectomy pad 30 includes a seamless molded outer casing, which is generally indicated at 43, and which is formed of KODEL, or like brand, of high-loft bonded polyester non-woven fibrous material components, as will be described hereinafter, which has a hollow generally conical-shaped internal cavity 83 (FIG. 4), and is covered by a protective fabric outer cover 44 which is formed of a molded outer or front panel 45 (FIG. 13) and an inner flat or body side panel 46 (FIG. 15) which are formed of ARNEL tricot, or like fabric, and which are stitched together along their outer marginal edge portions and to the outer marginal edge portions of the seamless molded fibrous material outer casing 43, as at 47 (FIG. 2 and 4).

The seamless molded fibrous material outer casing 43, which is formed of high-loft bonded KODEL, or like brand of polyester fibrous non-woven material, is shaped and molded to provide (1) a generally conical-shaped seamless molded front ot outer side portion 48 (FIG. 4) which is adapted to fit into and fill out a brassiere cup, as 31, to simulate the conical shape of a woman's breast which has been removed surgically; and (2) a laterally extending tongue portion 49 which is also adapted to fit into a brassiere, or like garment, but extends outwardly from the conical-shaped front or outer side portion 48 to fit into the underarm area from which tissue has been removed in the surgical mastectomy operation; and the protective outer fabric cover 44 is similarly shaped and formed to cover the seamless molded outer fibrous material casing 43 (FIGS. 2, 3 and 4) and has a seamless front or outer surface (FIG. 2).

The seamless molded fibrous material outer casing 43 is formed of a first or outer and die-cut circular panel 50 of high-loft bonded KODEL, or like brand, of polyester non-woven fibrous material (FIG. 8) which is preferably formed of a relatively thick circular panel, such as 6-ounce high-loft bonded KODEL polyester non-woven fibrous material and is sized and trimmed on a master pattern which is not incorporated in the complete and assembled mastectomy pad 30.

Figure 10:
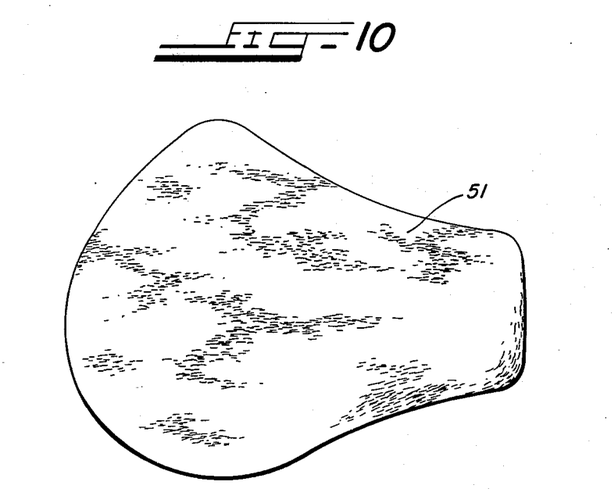
FIG. 10 is a plan view of a die-cut panel of polyester fibrous material which forms the inner or body side component of the seamless molded polyester fibrous material outer casing in the preferred embodiment of the new mastectomy pad.
Figure 11:
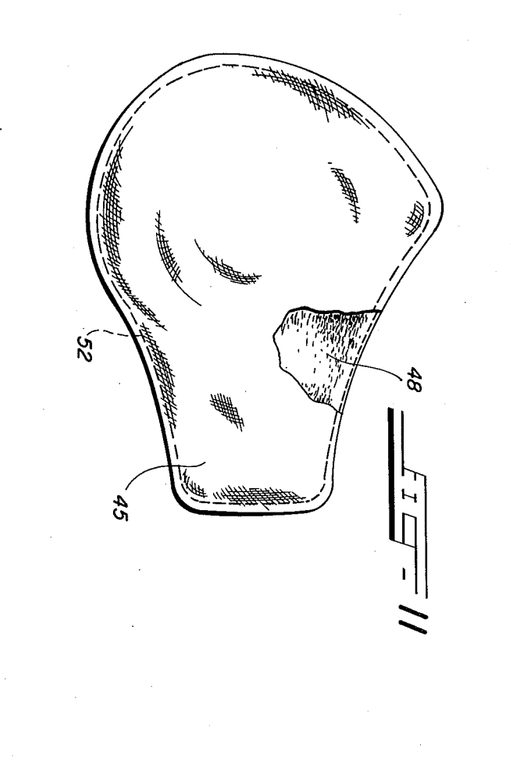
FIG. 11 is a top plan view of the front or outer side component of the preferred embodiment of the new mastectomy pad with a part of the front or outer panel of the protective outer cover broken away to reveal the stitching around the marginal edge portions of the front or outer side component of the seamless molded fibrous material outer casing.
Figure 12:
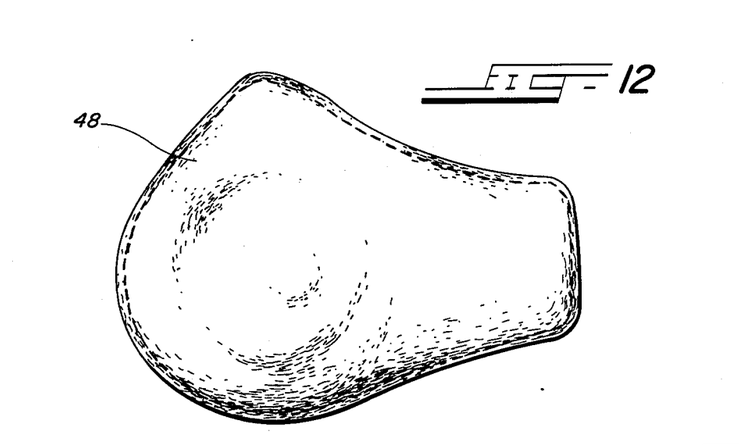
FIG. 12 is a top plan view of a blank or panel from which the molded seamless front or outer side component of the seamless molded polyester fibrous material outer casing is formed.
Figure 13:
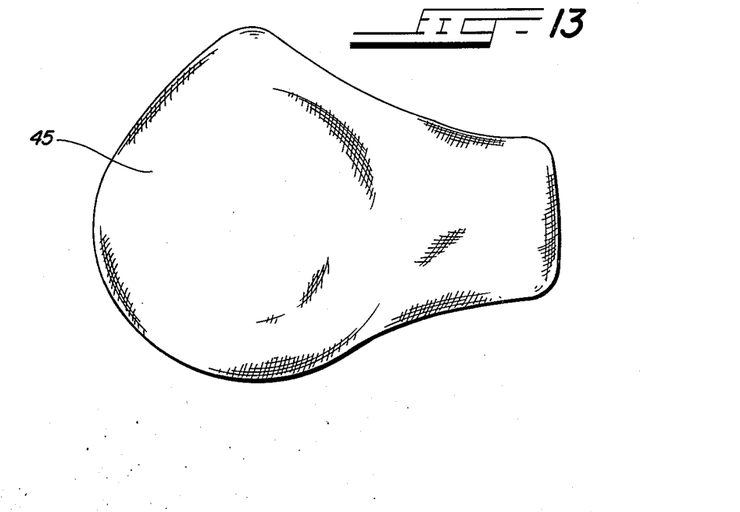
FIG. 13 is a top plan view of the front or outer side panel of the protective outer fabric cover.

The seamless molded fibrous material outer casing 43 also includes an inner or body side panel 51 which is preferably formed of 3-ounce high-loft bonded KODEL, or like brand, of polyester non-woven fibrous material cut into the form and shape shown in FIG. 10.

Figures 14, 15, 16, 17, 18, 19, 20:
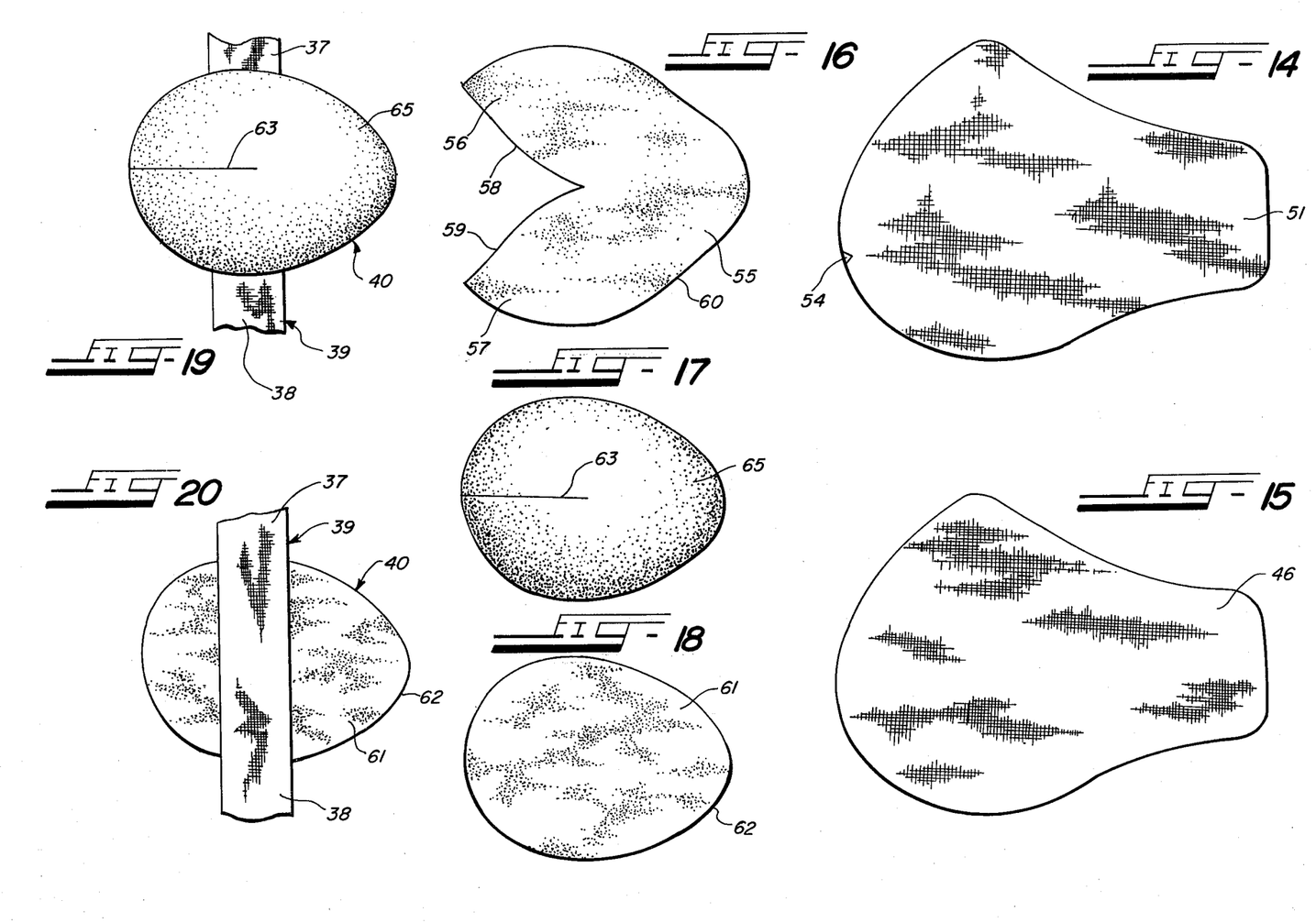
FIG. 14 is a top plan view of the inner or body side panel or component of the seamless molded polyester fibrous material outer casing.
FIG. 15 is a top plan view of the inner or body side panel of the protective fabric outer cover of the new mastectomy pad.
FIG. 16 is a top plan view of a blank or panel of foam rubber which forms the front or outer side of the weighted foam rubber internal casing which is embodied in the new mastectomy pad.
FIG. 17 is a top plan view of the foam rubber blank or panel shown in FIG. 16 formed to provide the front or outer side of the foam rubber internal casing.
FIG. 18 is a top plan view of a blank or panel of foam rubber which provides the inner or body side of the foam rubber internal casing.
FIG. 19 is a top plan view of the weighted foam rubber internal casing with the non-stretchable attaching strap and attaching loops attached thereto, as seen from the front or outer side thereof.
FIG. 20 is a rear or body side plan view of the foam rubber internal casing and non-stretchable attaching strap and attaching loops, shown in FIG. 19, as seen from the inner or body side thereof.

In the manufacture of the preferred embodiment of the new mastectomy pad, as illustrated in FIGS. 1 to 20, inclusive, of the drawings, the relatively thick circular panel 50 (FIG. 8) of preferably 6-ounce high-loft KODEL polyester non-woven fibrous material is molded in a heated mold, such as is disclosed in applicant's U.S. Pat. No. 3,597,800 granted Aug. 10, 1971 and entitled "Apparatus for Making Brassiere Pads," to provide the generally conical-shaped front or outer side portion 48 and the laterally projecting tongue portion 49 (FIGS. 4 and 9); the thus molded polyester non-woven fibrous material panel 48-49 being stitched along it outer marginal edges, as at 52 (FIGS. 9 and 11), and being somewhat reduced in thickness along its outer marginal edge portions, as at 53, compared to the thickness of the remaining parts of the front or outer side portion 48 and the laterally projecting tongue portion 49 (FIG. 4). As shown in FIG. 14, the inner or body side polyester fibrous material panel 51 of FIG. 10 is provided along its marginal outer edge with a locator dart 54 to guide the seamstress in stitching the parts together, as at 47 (FIG. 4).

The resilient weighted closed foam rubber material casing 40 is arranged within the generally conical-shaped internal cavity 83 in the seamless molded fibrous material outer casing 43 (FIG. 4), and is formed from a first and outer panel 55 of foam rubber, which is die-cut into the form and shape shown in FIG. 16 and which includes parts 56 and 57 which have converging marginal edges, 58 and 59, respectively, which, in turn, merge into the outer marginal edge 60 of the die-cut foam rubber panel 55 (FIG. 16). The weighted foam rubber internal casing 40 also includes a second die-cut foam rubber panel 61 which forms the inner or body side component of the weighted foam rubber internal casing 40, and is die-cut into the shape and form in which it is shown in FIGS. 4, 18 and 20, and has an outer marginal edge 62.

In forming the resilient weighted foam rubber internal casing 40 the die-cut foam rubber panel 60 (FIG. 16) is formed into the form and shape in which it is shown in FIGS. 4, 6, 17, 18 and 19, to provide therein a generally conical-shaped internal cavity 84 (FIG. 4), and during this operation the marginal edge portions 58 and 59 thereof are brought together, along a line of union 63, where they are adhesively secured together by means of a suitable rubber cement, or like adhesive. In this manner, the foam rubber blank 55 is shaped and formed to provide the generally conical-shaped front or outer component 65 of the foam rubber internal casing 40 which conforms generally to the conical shape and curvature of the front or outer side 48 of the seamless molded outer fibrous material casing 43 and is completely enclosed thereby (FIG. 4).

After the front or outer foam rubber component 65 of the foam rubber internal casing 40 has been formed into the desired shape, as in FIGS. 4, 6, 17 and 19, the inner or body side foam rubber panel or component 61 and the front or outer side panel or component 65 are adhesively secured thereto, by means of a suitable rubber cement, or the like, along their marginal edge portions. However, during this operation a filler opening 67 is provided, or left open, through which a body or mass 68 of filler material is poured into the internal cavity 84 in the foam rubber internal casing 40 to provide weight means therein. A preferred form of this filler material 68 consists of a mixture of finely divided particles 69 of shredded foam rubber and finely divided particles of weight-enhancing material in the form of sand 70. The filler opening 67 is then closed by completing the cementing of the marginal edge portions of the foam rubber panels or components 65 and 61 together, as at 66 (FIG. 7).

It has been found that the preferred embodiment 30 of the new mastectomy pad has the desirable advantages and characteristics over the prior art, as exemplified by the applicant's earlier U.S. Pat. Nos. 2,482,297 and 3,278,947, as hereinbefore set forth, including flexibility; resiliency; ability to withstand repeated washings over prolonged periods of time; ability to be easily and readily fastented in position of use to a shoulder strap and to the underband of a brassiere or garment worn by the user and when so attached will not shift or move from its proper position of use, due to the weighted foam rubber internal casing 40 and the non-stretchable fabric attaching means or top and bottom attaching loops 37 and 38; will readily conform to the shape of the foam rubber internal casing 40 to fill out and adapt itself to the shape of brassiere cups of various shapes; is completely free of any visible or otherwise discernible seam or stitching across or over the front surface or outer side of the front or outer panel or component 48-49 of the molded seamless polyester fibrous material outer casing 43, as shown in FIG. 4, so that no objectionable seam or stitching is visible or otherwise discernible from the front or outer side of the brassiere or garment in which the new mastectomy pad 30 is used; and may readily be removed from position of use for washing or other purposes.

It will be noted (FIG. 3) that the new mastectomy pad 30 bulges somewhat inwardly at the body side thereof so that when the new mastectomy pad 30 is in use it fits firmly but gently and softly against the body side of the brassiere cup in which it is worn while, at the same time, the resilient and compressible nature of the weighted foam rubber internal casing 40, and the soft, resilient nature of the seamless molded polyester fibrous material outer casing 43 enable the new mastectomy pad to adjust itself readily to brassiere cups of varying shapes.

THE MODIFICATION ILLUSTRATED IN FIGS. 21 TO 24, INCLUSIVE, OF THE DRAWINGS

A modification of the invention is illustrated in FIGS. 21 to 24, inclusive, of the drawings, wherein it is generally indicated at 71 (FIG. 24), and those parts thereof which are similar or comparable to corresponding parts in the preferred embodiment of the invention illustrated in FIGS. 1 to 20, inclusive, have been given the same reference numerals followed by the additional and distinguishing reference character "a."

Figures 21, 22, 23, 24:
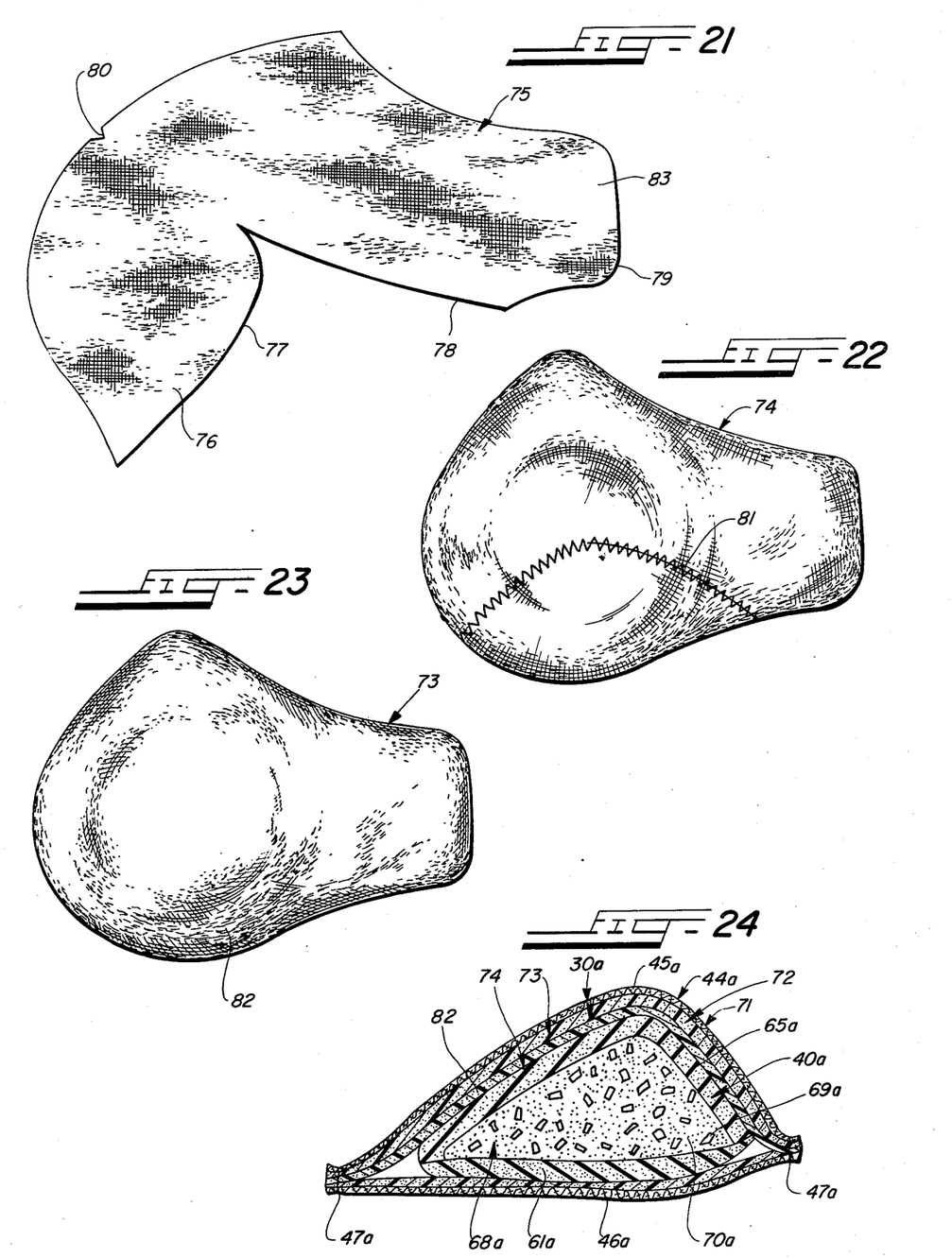
FIG. 21 is a top plan view of a blank or panel of high-loft bonded polyester fibrous material which is employed to form an intermediate member which is arranged between the front or outer side of the fibrous material outer casing and the foam rubber internal casing in a modified form of the invention.
FIG. 22 is a top plan view of the fibrous material blank or panel shown in FIG. 21 formed and stitched to form the intermediate member in the modified form of the invention.
FIG. 23 is a top plan view of a blank or polyester fibrous material which forms the front or outer side of the polyester fibrous material outer casing in the modified form of the invention.
FIG. 24 is a central longitudinal sectional view of a mastectomy pad embodying the modified form of the invention.

The modification of the invention illustrated in FIGS. 21 to 24, inclusive, of the drawings, differs from the preferred embodiment of the invention illustrated in FIGS. 1 to 20, inclusive, in that in this modification of the invention the front or outer side of the seamless molded high-loft bonded polyester non-woven fibrous material outer casing 72, which encloses the weighted foam rubber internal casing 40a, includes a front or outer panel 73 behind or inwardly of which is an intermediate member or panel 74, as shown in FIG. 24, and which is arranged inwardly of and immediately behind the front or outer panel 73 of the seamless molded outer casing 72.

Thus, in the modification of the invention illustrated in FIGS. 21 to 24, inclusive, the front or outer panel 73 of the seamless molded fibrous material outer casing 72 is molded in the form of a panel 82 of preferably 3-ounce KODEL, or like brand, of high-loft bonded non-woven polyester fibrous material into the shape and form in which it is shown in FIG. 23, and the intermediate member 74 is formed from a panel or blank 75 of 3-ounce KODEL, or like brand, of high-loft bonded polyester non-woven fibrous material, as shown in FIG. 21, which includes two parts 76 and 83 which have converging marginal edges 77 and 78, respectively, which merge into the marginal edge 79 of the blank or panel 75 which is provided with a locator dart 80 for the guidance of the seamstress. The intermediate member 74 is then completed by stitching the parts 76 and 83 of the blank or panel 75, together, as at 81 (FIG. 22), into the form in which it is shown in FIGS. 22 and 24 to provide the intermediate member 74.

The modified form 30a of the new molded polyester fibrous material mastectomy pad is then completed by assembling the parts thereof together, as shown in FIG. 24.

In the manufacture of the modification of the invention illustrated in FIGS. 21 to 24, inclusive, of the drawings, the intermediate member 74 serves as a master pattern for shaping and sizing the front or outer panel 73 of the seamless molded outer fibrous material casing 72 and the intermediate member 74 is incorporated in the completed mastectomy pad 30a wherein it cooperates with the 3-ounce high-loft bonded polyester non-woven fibrous material outer or front panel 73 of the seamless molded fibrous material outer casing 72 to provide a 6-ounce body of high-loft bonded polyester non-woven fibrous material under the front or outer panel of the protective outer fabric cover 44a and between the latter and the front or outer panel 65a of the foam rubber internal casing 40a, as shown in FIG. 24. However, in the preferred form of the invention illustrated in FIGS. 1 to 20, inclusive, the single front or outer panel 48 of the seamless molded outer fibrous material casing 43 is, per se, preferably 6-ounce high-loft bonded polyester non-woven fibrous material, and the master pattern from which it is sized and shaped is not incorporated in the completed mastectomy pad, as shown in FIG. 4.

The modification 30a of the invention illustrated in FIGS. 21 to 24, inclusive, has all of the advantages and characteristics of the preferred embodiment 30 of the invention illustrated in FIGS. 1 to 20, inclusive, except for the use of the intermediate member 74 which has the seam 81 which may be manually felt even though not seen or visible through the front or outer panel 73 of the seamless molded outer casing 72 and which may, for this reason, in some instances, be objectionable to some users of the modified form of the new mastectomy pad 30a shown in FIGS. 21 to 24, inclusive.

The term "loft," as used herein and in the claims, is defined in *Webster's Third New Dictionary* (G & C Merriam Company, Springfield, Mass.) (Copyright 1961) at page 1330, under Definition No. 6, as follows:

"The resiliency of textile fibers, esp. wool."

*Random House Dictionary* (Unabridged) (Copyright 1976) (Random Hose, New York, N.Y.) defines the word "loft" at Page 842, under Definition No. 6, as follows:

"Loft—the resilience of wool."

A brochure of Eastman Chemical Products, Inc. of Kingsport, Tenn. (Tennessee Eastman) identified as No. K181D, dated May 19, 1975, and entitled "Guide to KODEL Polyester Textile Fibers," defines various types of polyester textile fibers under the heading "KODEL Type Numbers," including the following: "KODEL 431—High-permanent-crimp fiber with good resilience, loft, fluffiness and filling power."

It will thus be seen from the foregoing description, considered in conjunction with the accompanying drawings, that the present invention provides a new and improved mastectomy pad having the desirable advantages and characteristics and accomplishing it intended objects including those hereinbefore pointed out and others which are inherent in the invention.

I claim:

1. A mastectomy pad comprising
   a. a seamless molded outer casing molded of high-loft bonded polyester non-woven fibrous material and having
      1. an outer marginal edge portion;
      2. an inner or body side panel;
      3. a front or outer panel including
         a. a generally conical-shaped body portion;
         b. the said seamless molded outer casing being adapted to fit into and to be worn in and to fill out the breast cup of a brassiere or garment by a woman who has had a mastectomy operation, and having therein
            1. a hollow generally conical-shaped internal cavity and including
      4. a tongue portion projecting laterally from the said body portion and which in use is adapted to extend outwardly over the underarm area of the user from which tissue has been removed as an incident to a mastectomy operation;
   b. a closed and generally conical-shaped foam rubber internal casing arranged in and enclosed within the said internal cavity in the said seamless molded fibrous material outer casing and including
      1. an outer marginal edge portion; and having therein
      2. a generally conical-shaped internal cavity;
   c. weight means in the form of a body of filler material arranged in the said generally conical-shaped internal cavity in the said closed foam rubber internal casing; and
   d. a protective fabric outer cover arranged over and outwardly of and enclosing the said seamless molded outer casing of fibrous material and having
      1. an outer marginal edge portion;
   e. the said seamless molded outer casing of high-loft bonded polyester non-woven fibrous material and the said protective outer fabric cover being stitched together along their said outer marginal edge portions outwardly of the said outer marginal edge portion of the said closed and generally conical-shaped foam rubber internal casing.

2. A mastectomy pad as defined in claim 1 in which
   a. the said body of filler material arranged in the said generally conical-shaped internal cavity in the said closed foam rubber internal casing is comprised of a mixture of 1. a mass of shredded foam rubber; and
2. finely divided particles of weight-enhancing material.

3. A mastectomy pad as defined in claim 1 in which
  a. the said body of filler material arranged in the said generally conical-shaped internal cavity in the said closed foam rubber internal casing is comprised of a mixture of
   1. a mass of shredded foam rubber; and
   2. particles of sand intermixed with the said mass of shredded foam rubber.

4. A mastectomy pad as defined in claim 1 which includes
  a. non-stretchable fabric attaching means attached to the said closed foam rubber internal casing and including
   1. a first and non-stretchable attaching portion projecting upwardly from the top of the said mastectomy pad and adapted to be attached to the shoulder strap of a brassiere or garment worn by the user of the said mastectomy pad; and
  b. a second non-stretchable attaching portion projecting downwardly from the bottom of the said mastectomy pad and adapted to be attached to the underband of a brassiere or garment worn by the user of the said mastectomy pad.

5. A mastectomy pad as defined in claim 4 in which
  a. the said first and the said second non-stretchable attaching portions of the said non-stretchable fabric attaching means are in the form of attaching loops.

6. A mastectomy pad as defined in claim 5 in which
  a. the said attaching loops are stitched to and between the said outer marginal edge portion of the said seamless molded fibrous material outer casing and the said marginal edge portion of the said protective fabric outer cover.

7. A mastectomy pad as defined in claim 6 in which
  a. the said non-stretchable fabric attaching means is adhesively attached to the said closed foam rubber internal casing.

8. A mastectomy pad as defined in claim 1 in which
  a. the said protective fabric outer cover includes
   1. a seamless front or outer panel; and in which
  b. the said front or outer panel of the said seamless molded fibrous material outer casing is composed of
   1. a single panel of the said high-loft bonded polyester non-woven fibrous material arranged between the said seamless outer panel of the said protective fabric outer cover and the said foam rubber internal casing and having
    a. a seamless front or outer surface facing toward and lying immediately inwardly of the said front or outer panel of the said protective fabric cover.

9. A mastectomy pad as defined in claim 1 which includes
  a. an intermediate member of high-loft bonded polyester non-woven fibrous material formed into the generaly shape of the said front or outer panel of the said seamless molded outer casing and arranged between the said front or outer panel of the said seamless molded outer casing and the said closed and generally conical-shaped foam rubber internal casing.

10. A mastectomy pad as defined in claim 9 in which
  a. the said intermediate member is formed of a blank or panel of the said high-loft bonded polyester non-woven fibrous material having integral portions which are stitched together across the said blank or body thereof to provide
   1. a generally conical-shaped body portion; and
   2. a laterally projecting tongue portion.

* * * * *